United States Patent [19]

Fujiwa et al.

[11] Patent Number: 5,378,736

[45] Date of Patent: Jan. 3, 1995

[54] COMPOSITION COMPRISING NOVEL ALICYCLIC COMPOUND, PROCESS FOR PREPARATION THEREOF, CURABLE COMPOSITION, AND PHOTO-POLYMERIZABLE COMPOSITION

[75] Inventors: Takaaki Fujiwa, Hiroshima; Shoji Watanabe, Shizuoka; Shin Takemoto; Yoshiyuki Harano, both of Hiroshima, Japan

[73] Assignee: Daicel Chemical Industries, Ltd., Osaka, Japan

[21] Appl. No.: 707,736

[22] Filed: May 30, 1991

[30] Foreign Application Priority Data

May 30, 1990 [JP] Japan ................... 2-140732
Jun. 15, 1990 [JP] Japan ................... 2-157062
Aug. 17, 1990 [JP] Japan ................... 2-216569

[51] Int. Cl.⁶ .............. C08G 63/08; C08G 59/24; C07D 301/14; C07C 69/76
[52] U.S. Cl. .................. 522/170; 528/271; 528/354; 549/525; 560/8
[58] Field of Search .............. 522/170; 528/271, 354; 560/8; 549/525

[56] References Cited

U.S. PATENT DOCUMENTS 3,658,669  4/1972  Colomb, Jr. et al. ......... 522/142
4,629,779  12/1986 Koleske ..................... 522/170
4,849,532  7/1989  Beohme et al. .............. 549/525

FOREIGN PATENT DOCUMENTS 3528004  2/1987 Germany ................... 549/525
2164675  7/1987 Japan ..................... 549/525

*Primary Examiner*—Susan W. Berman
*Attorney, Agent, or Firm*—Sughrue, Mion, Zinn, Macpeak & Seas

[57] ABSTRACT

Disclosed are a composition and a process for preparation thereof, which composition comprises a novel alicyclic compound and an epoxidized compound thereof represented respectively by formulae (I) and (II)

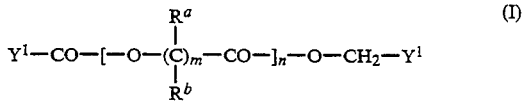

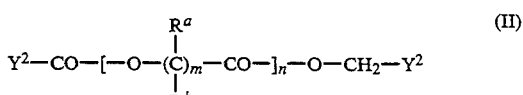

wherein $Y^1$ represents at least one of the structural groups

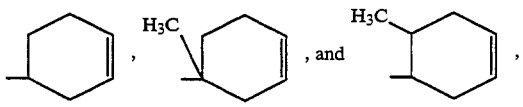

$Y^2$ represents at least one of the the structural groups

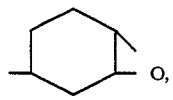

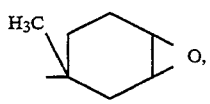

and

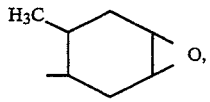

$R^a$ and $R^b$ each represent hydrogen or a methyl group, m represents a natural number of from 1 to 7, and n represents a natural number of from 1 to 20.

The composition (II) is a multi-functional alicyclic epoxidized compound, which has a property of being high in epoxy group density in a molecule compared with alicyclic conventional epoxy resins which can provide resins having wide range properties from being hard to being soft.

10 Claims, 5 Drawing Sheets

COMPOSITION COMPRISING NOVEL ALICYCLIC COMPOUND, PROCESS FOR PREPARATION THEREOF, CURABLE COMPOSITION, AND PHOTO-POLYMERIZABLE COMPOSITION

FIELD OF THE INVENTION

The present invention relates to a composition which comprises a novel lactone-modified alicyclic compound, a novel epoxidized compound thereof and also relates to a process for the preparation thereof, and further relates to a curable composition and a photo-polymerizable composition.

BACKGROUND OF THE INVENTION

Hitherto, the alicyclic epoxy resin

(wherein $Y^2$ represents at least one group selected from

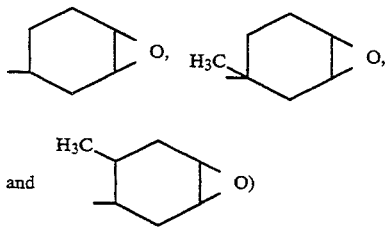

has been well-known, and has been used as a component of a composition for coating, or a material for electric fields, which was used by curing with a polymeric compound having carboxyl groups, hydrides thereof, or a compound having hydroxyl groups and or amino groups, and or with a curing agent.

However, the alicyclic epoxy resin (IV) can not provide a polymeric diepoxide by curing with the above described polymeric compound.

Furthermore, the epoxy groups of the alicyclic epoxy resin have a disadvantage of being low in reactivity because of the short intramolecular distance between its ester group and its epoxy group.

On the other hand, the compound (V)

$$Y^2-CH_2-O-CO-C(CH^2)_4-COO-CH_2-Y^2 \quad (V)$$

(wherein $Y^2$ represents at least one group selected from

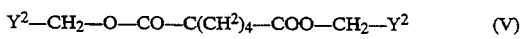

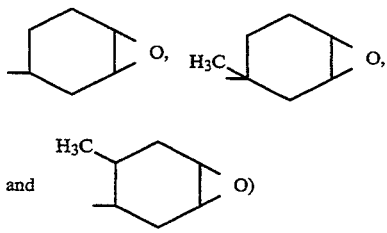

has also been used in the same fields of uses as described hereinabove.

However, the alicyclic epoxy resin (V) lacks flexibility, being a monomer not having a molecular weight distribution such as an oligomer. As a result of an intensive investigation, the inventors of this invention have now found that it is possible not only to solve the problems as described hereinabove, but also to add flexibility, reactivity, and heat resistance in epoxy resins.

SUMMARY OF THE INVENTION

The present invention was developed as a result of an intensive investigation in order to develop an excellent component for a coating composition, a curable composition, and a photo-polymerizable composition.

It is a primary object of the present invention to solve the problems of the conventional compositions for coating, particularly insufficient reactivity and insufficient toughness of the coating layers. There is provided a composition and a process for preparation of said composition consisting essential of a compound represented by formula (I)

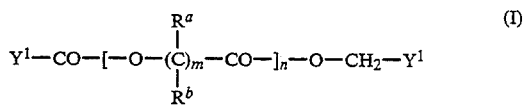

wherein $Y^1$ represents at least one of the structural groups

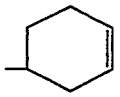

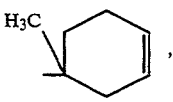

and

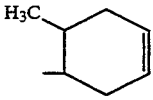

$R^a$ and $R^b$ each represents hydrogen or a methyl group, m represents a natural number of from 1 to 7, and n represents a natural number of from 1 to 20.

The present composition has excellent properties capable of being used as a resin component, particularly an epoxy resin component for coating materials, such as a composition for an electrodeposition coating, a powder composition for coating, a baking composition for coating having a high solid content, etc.

Furthermore, the present composition can be used as a composition capable of curing at low temperature conditions by an addition to a composition composed of a polysiloxane type macromonomer and an organic aluminum or a chelate compound of an organic zirconium compound to obtain an excellent outer appearance and an excellent ductility of the coating layers.

DETAILED DESCRIPTION OF THE INVENTION

Figure 1:
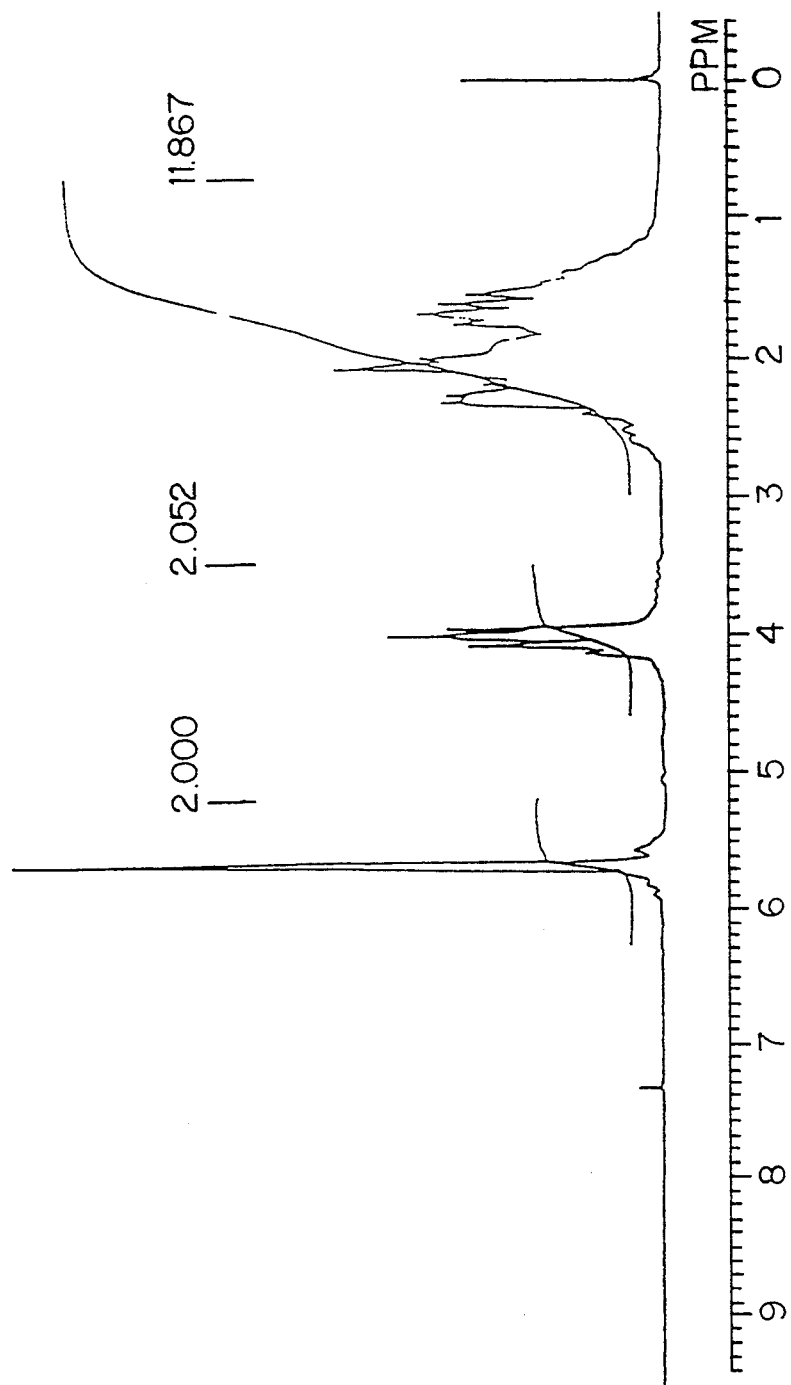
FIG. 1 is a $^1$H-NMR(Nuclear Magnetic Resonance) chart.

The present invention is described hereinafter in more detail.

According to a first aspect of the present invention, there is provided a composition comprising, and preferably consisting essentially of, an alicyclic compound represented by general formula (I) described hereinafter.

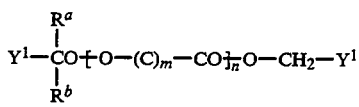     (I)

In formula (I),

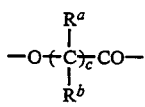

is a lactone unit, $Y^1$ represents at least one group of

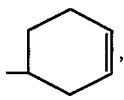

derived from 1,2,5,6-tetrahydrobenzyl-1,2,5,6-tetrahydrobenzoate,

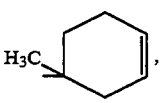

derived from 1-methyl-1,2,5,6-tetrahydrobenzyl-1-methyl-1,2,5,6-tetrahydrobenzoate, and

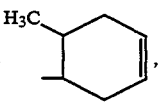

derived from 6-methyl-1,2,5,6-tetrahydrobenzyl-6-methyl-1,2,5,6-tetrahydrobenzoate represented by formula (III).

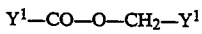     (III)

1,2,5,6-tetrahydrobenzyl-1,2,5,6-tetrahydrobenzoate, 1-methyl-1,2,5,6-tetrahydrobenzyl-1-methyl-1,2,5,6-tetrahydrobenzoate and 6-methyl-1,2,5,6-tetrahydrobenzyl-6-methyl-1,2,5,6-tetrahydrobenzoate, can be prepared by an esterification reaction according to so-called Tischenko reaction of tetrahydrobenzaldehyde, 1-methyl-1,2,5,6-tetrahydrobenzaldehyde and 1-methyl-1,2,5,6-tetrahydrobenzaldehyde, respectively, on a commercial basis, as a starting material for the preparation of compound (IV).

Tetrahydrobenzaldehyde, 1-methyl-1,2,5,6-tetrahydrobenzaldehyde and 1-methyl-1,2,5,6-tetrahydrobenzaldehyde can be prepared on a commercial basis by a Diels-Alder reaction of butadiene with acrolein, methacrolein, and crotonaldehyde, respectively.

In formula (I), $R^a$ and $R^b$ each represent hydrogen or methyl group, respectively, which are exchangeable with each other, depending upon starting lactone compounds.

For example, in the case that epsilon-caprolactone is used as the starting material, $R^a$ and $R^b$ represent hydrogen.

Further, in the case that beta-methyl-delta-valerolactone is used as the starting material, $R^a$ and $R^b$ represent methyl group or hydrogen, respectively.

In addition, in the case that 3-methyl-caprolactone is used as a starting material, $R^a$ and $R^b$ represent methyl group and hydrogen, respectively.

c, which represents a natural number of from 1 to 7, is also decided depending upon the starting lactone compounds.

For example, in the case that epsilon-caprolactone, beta-methyl-delta-valerolactone or cyclooctanone lactone are used as the starting material, c is 5, 4 or 7, respectively.

n corresponds to a mol number of the lactone compound introduced into the alicyclic compound (I), which is a natural number of larger than 0.

In the case that a lactone compound is not introduced, the mol number n is 0, for example, if 5 mols of the lactone compound are introduced, the mol number n is inevitably 5.

It is noted that epsilon-caprolactone can be prepared by a Baeyer-Villiger reaction, in which cyclohexanone is oxidized by a peracid, etc., on a commercial basis.

Furthermore, it is noted that trimethylcaprolactone can be prepared on a commercial basis by a Baeyer-Villiger reaction, in which trimethylcyclohexanone is oxidized by a peracid, etc.

Still further, it is noted that trimethylcyclohexanone can be prepared on a commercial basis by a hydrogenation reaction of isophorone, followed by a Baeyer-Villiger reaction to obtain trimethylcaprolactone with a peracid.

Beta-methylgamma-valerolactone can be manufactured from 2-hydroxy-4-methyltetrahydropyran as a starting material.

Examples of the peracid include, for example, an organic carboxylic peracid such as performic acid, peracetic acid, perpropionic acid, perbenzoic acid, m-chloroperbenzoic acid, etc., or peracetic acid produced by acetic acid and hydroperoxide or produced by acetic anhydride and sulfuric acid.

According to a second aspect of the present invention, there is provided a process for the preparation of a composition consisting essentially of an alicyclic compound represented by formula (I), which process comprises an addition reaction of a compound represented by formula (III)

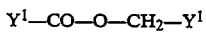     (III)

wherein $Y^1$ represents at least one of the structural group

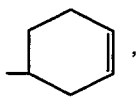

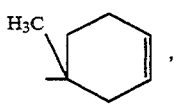

and

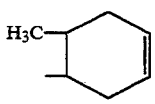

with a lactone compound under the presence of a catalyst.

Reaction conditions for introducing lactone units into the compound (III) are described in more detail below.

1 mol of the compound (III) is allowed to react with a fixed amount of a lactone compound, such as from 1 to 20 mols, and preferably from 1 to 10.

Where the molar ratio is more than 20, the resulting compound (I) can not provide a resulting epoxy resin having sufficiently excellent properties; for example, the epoxy resin is too soft.

On carrying out the reaction for introducing lactone units into the compound (III), a catalyst can be used.

Effective catalysts include an organic tin compound such as stannous or stannic octylate, dibutyl tin oxide, and dibutyl tin laurate, etc., a halogenated tin compound such as stannous chloride, stannous bromide, stannous iodide, etc.

For the purpose of an activation of the catalyst to be used, an organic acid such as formic acid, acetic acid, propionic acid, etc., can be used together with the catalyst.

Furthermore, a heteropoly-acid such as phosphorous tungstic acid, a tungstic silicate, etc., can also effectively be used as the catalyst.

Still further, a metal compound such as magnesium chloride, magnesium methoxide, magnesium ethoxide, aluminum isopropoxide, aluminum xanthoxide, tetrabutyl titanate, tetrapropyl titanate, tetraethoxy titanate, etc., can be used as the catalyst.

The amount of the catalyst to be used is preferably from 1,000 ppm to 0.1 ppm, more preferably from 200 to 0.1 ppm based on the total amount of the starting materials.

Where the amount is more than 1,000 ppm, the reaction velocity is high. However, the final product may be undesirably colored in the case of not being removed.

On the other hand, where the amount is less than 0.1 ppm, there is required an uneconomically long period of time in order to complete the reaction, because the catalytic effect is too low.

The reaction for introducing lactone units into the compound (III) can be preferably carried out at a temperature of from 100° to 250° C.

Where the temperature is lower than 100° C., the reaction velocity is low. On the other hand, where the temperature is higher than 250° C., coloring of the resulting product is significant, and there results a tendency to readily undergo an undesirable decomposition reaction, The reaction can be carried out either in the absence or the presence of a solvent such as toluene, xylene and or an inert solvent not having an active hydrogen, such as a hydrocarbon or the like, having high boiling temperatures.

In the case that the reaction is carried out at the absence of a solvent, the resulting products can be diluted by various solvents in order to lower viscosity thereof, thereby rendering such capable of easy handling.

The reaction can be surprisingly carried out at the presence of minor amount of a compound having hydroxyl group, thereby being capable of considerably increasing the reaction velocity.

The compound having hydroxyl group includes water, methanol, ethanol, propanol, butanol, ethyleneglycol, diethyleneglycol, triethyleneglycol, propyleneglycol, butanediol, pentanediol, neopentylglycol, 1,6-hexanediol, 3-methylpentanediol, trimethylolpropane, glycerine, trimethylolethane, pentaerythritol, etc.

The compound is preferably used in an amount so as to provide a hydroxyl value of the resulting compound (I) in a range of from 0.01 to 50, and more preferably from 0.1 to 10.

Where the hydroxyl value is adjusted to less than 0.01, effects due to the use of the compound are low.

On the other hand, where the hydroxyl value is adjusted to more than 50, the properties tend to deteriorate in spite of the higher effect.

Charging methods of the starting materials are not limited; for example, any charging order may be used for the starting compound (III), a lactone compound, a catalyst, and a reaction promoter which is a compound having hydroxyl groups described hereinabove.

The catalyst can be charged in the form of a solution dissolved in other starting material such as the lactone compound, especially when used in a minor amount, such as a few ppm, which is difficult to charge, in the reaction solution.

The reaction is preferably carried out under the presence of nitrogen gas.

Although the presence of oxygen in the reaction vessel does not affect reaction velocity, the resulting product unpreferably has a tendency of being colored, and a gaseous composition atmosphere of possibly explosive range is undesirably formed in the space of the reaction vessel.

It is supposed that the resulting crude solution after the completion of the reaction contains mainly compound represented by formula (I), and contains small or minor amounts of various compounds which are by-products and unreacted starting materials.

For example, in the case that one mol of the compound (III) is allowed to react with $n1+n2+n3+n4+n5+n6$ mols of a lactone compound in the presence of a catalyst and a reaction promoter, which is a diol compound represented by formula $HO—R^x—OH$, the resulting product is a mixture composed of the following compounds;

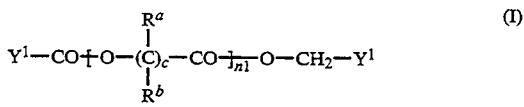

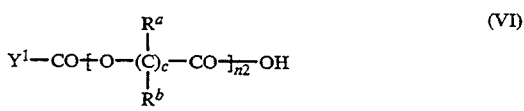

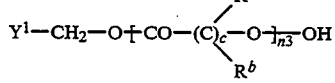 (VII)

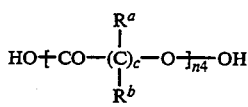 (VIII)

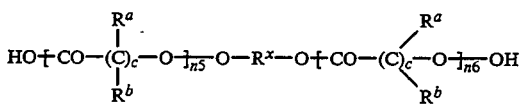 (IX)

In formula (I), (III), (VI), (VII), (VIII), and (IX),

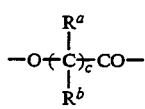

is a lactone unit depending upon a lactone compound to be used, $Y^1$ represents at least one selected from

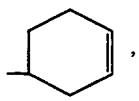,

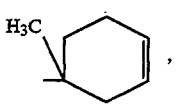, and

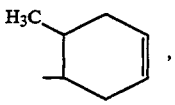, $R^a$ and $R^b$ each represents hydrogen or methyl group (i.e., the groups are exchangeable with each other), which depend upon the starting lactone compounds.

c, which represents a natural number of from 1 to 7, is also decided depending upon the starting lactone compounds to be used.

n1+n2+n3+n4+n5+n6 corresponds to the total mol numbers of the lactone compound introduced into the starting alicyclic compound (III), which is inevitably nearly equal to the mol numbers of the charged lactone compound, which is preferably a natural number of from 1 to 20.

In the case that n1 is 0 in formula (I), the compound corresponds to the compound (III), which is the unreacted starting material.

The resulting product is a mixture composed of the lactone adducts having various mol numbers, that is, n1, n2, n3, n4, n5 and n6 have a distribution in a range of n1-n6=0, 1, 2, 3, ... L, respectively.

The main component or primary component in the mixture is compound (I).

The resulting product can be used, for example, as a component of coating compositions without carrying out any purification or separation.

Furthermore, the resulting product can also be used after optionally carrying out a purification or separation.

For example, the product can be washed with water in order to remove low molecular weight components having a hydroxyl group at a terminal position, and can also be separated by a chromatography.

Furthermore, the resulting product can also be used after diluting with a solvent.

In the case that epsilon-caprolactone is used as a lactone compound, all of the units

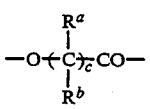

in (I), (VI), (VII), (VIII) and (IX) are —O—(—$CH_2$—)$_5$—CO—.

In the case that beta-methylgamma-valero-caprolactone is used as an actone compound, all the units

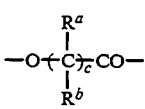

in (I), (VI), (VII), (VIII) and (IX) are

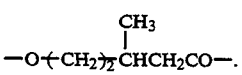.

In the case that 3,5,5-trimethylcaprolactone is used as a lactone compound, all the units

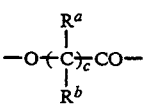

in (I), (VI), (VII), (VIII) and (IX) are

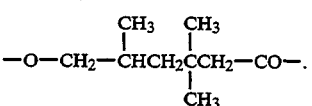

In the case that 3,3,5-trimethylcaprolactone is used as a lactone compound, all the units

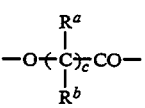

in (I), (VI), (VII), (VIII) and (IX) are

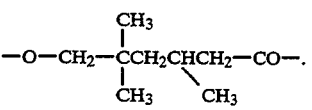

The lactone compound can also be used as a mixture composed of at least two kinds of lactones.

In the case that the mixed lactones are used as a lactone compound, the mixed lactone units are randomly introduced into the compounds (I), (VI), (VII), (VIII), and (IX).

According to a third aspect of the present invention, there is provided a composition consisting essentially of an epoxidized alicyclic compound represented by formula (II)

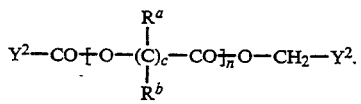  (II)

In formula (II),

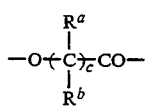

is a lactone unit; $Y^2$ represents at least one of the structural groups

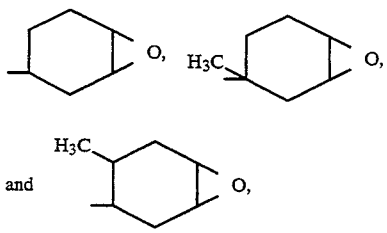

derived from an epoxidation reaction of the double bond in $Y^1$ described hereinabove; $R^a$ and $R^b$ each represents hydrogen or methyl group, depending upon the starting lactone compounds, as in the case of compound (I).

According to a fourth aspect of the present invention, there is provided a process for the preparation of a composition which comprises a compound represented by formula (II).

A composition consisting essentially of an epoxidized alicyclic compound represented by formula (II) can be prepared by an epoxidation reaction of a composition consisting essentially of an alicyclic compound represented by formula (I).

The epoxidation reaction can be carried out using an epoxidation agent such as a peracid or various hydroperoxides.

The peracids include performic acid, peracetic acid, perpropionic acid, perbenzoic acid, trifluoroperacetic acid, etc.

Of these peracids, peracetic acid is the preferred epoxidating agent, because it is available on an industrial basis at a moderate price and has a high stability.

The hydroperoxides include hydroperoxide, tertiary butylhydroperoxide, cumenperoxide, metachloroperbenzoic acid, etc.

When carrying out the epoxidation reaction, a catalyst can be used as appropriate to the circumstances.

For example, in the case that peracetic acid is used as an epoxidation agent, an alkali such as sodium carbonate, or an acid such as sulfuric acid, can be used as a catalyst.

Furthermore, in the case of using hydroperoxides, it is possible to obtain a catalytic effect, for example, using a mixture of tungstic acid and sodium hydroxide together with hydrogen peroxide, or hexacarbonylmolybudenum together with tertiary butyl hydroperoxide.

The epoxidation reaction is carried out in the absence or the presence of a solvent, while controlling the reaction temperature according to the apparatus to be used and the properties of the raw materials.

The temperature region of the epoxidation reaction can be selected according to the reactivity of the epoxidating agent.

In the case of peracetic acid, which is the preferable epoxidating agent, the preferred temperature is from 0° to 70° C.

If the temperature is under 0° C., the reaction velocity is slow, but if the temperature is over 70° C., a decomposition reaction of peracetic acid can occur.

In the case of tertiary butylhydroperoxide/molybdenumdioxide diacetyl acetate, which is an example of a hydroperoxide, the preferable temperature is from 200° C. to 150° C., based on the same consideration.

The use of solvents for dilution is effective for lowering the velocity of reaction of the raw materials and stabilizing the epoxidating agent.

In the case that peracetic acid is used as the epoxidating agent, preferred solvents include aromatic compounds, ether compounds, and ester compounds.

The molar ratio of the epoxidating agent to be used with respect to the unsaturated bonds is selected according to the proportion of the unsaturated bonds which it is desired to retain.

When preparing epoxy compositions having many epoxy groups, an equal or higher molar ratio of the epoxidating agents to the unsaturated bonds is preferably used, but using amounts of the epoxidating agents at a molar ratio of more than 10/1 with respect to the unsaturated bonds is not preferable, because of the cost and of the side reactions described hereinafter.

In the case of peracetic acid, a preferable molar ratio is 1/1 to 5-1.

Substituted groups are produced by the side reaction between epoxy groups and acetic acid is by-produced and contained in the desired product, depending upon the epoxidating conditions, with a generation of the epoxy groups from double bonds.

The product obtained also contains other minor by-products, by which a succeeding or a final product are affected adversely in color hue and acid value.

In order to prevent such adverse affects, additives as described hereinafter are preferably used also: phosphoric acid, potassium phosphate, sodium phosphate, ammonium hydrogenphosphate, pyrophosphoric acid, potassium pyrophosphate, sodium pyrophosphate, potassium 2-ethylhexyl pyrophosphate, sodium 2-ethylhexyl tripolyphosphate, potassium 2-ethylhexyl tripolyphosphate, tripolyphosphoric acid, potassium tripolyphosphate and or sodium tripolyphosphate, sodium 2-ethylhexyl tetrapolyphosphate, potassium 2-ethylhexyl tetrapolyphosphate, etc.

The use amount of the additives is generally from 10 ppm to 10,000 ppm, and preferably from 50 ppm to 1,000 ppm, based on the total weight of the starting materials.

It appears that the additives may have a chelating effect on metals which are derived from the reaction vessel or materials.

The metals are inactivated by the chelating effect.

The epoxidized product obtained can be separated from a crude reaction solution by various procedures, such as an extraction with water or aqueous alkali and a concentration step such as evaporation, etc. as described below.

For example, the reaction crude solution obtained can be used, with simple removal of solvents, etc., which are low boiling components, even without any purification process.

The removal of the low boiling components is carried out at a temperature of 50° to 200° C., and preferably 80° to 160° C.

Also, the degree of pressure reduction in the vessel can be adjusted depending upon boiling points of the solvents used in carrying out the epoxidation reaction.

After completion of the epoxidation reaction, flushing the crude solution with water is preferably carried out for the purpose of removing minor amounts of impure components.

When carrying out water flushing of the crude solution, an aromatic compound such as benzene, toluene, xylene, etc., a hydrocarbon such as hexane, heptane, octane, etc., an ester such as ethyl acetate, butyl acetate, etc., can also be used together with water.

The amount of water used on flushing is from 0.1 to 10 multiple amounts, preferably from 1 to 5 multiple amounts, based on the reaction crude solution volume.

Furthermore, an alkali aqueous solution can be used for the purpose of removal of minor amounts of acids, and then water can be used again in order to remove the alkali.

Specific preferred alkali includes NaOH, KOH, $K_2CO_3$, $Na_2CO_3$, $KHCO_3$, $NaHCO_3$ and $NH_3$. The concentration of the alkali can optionally be selected over a broad range.

The aqueous alkali leaching and succeeding water leaching can be carried out in a temperature range of from 10° to 90° C., and preferably is from 10° to 50° C.

After completion of water leaching and settling, the resultant organic layer is separated from water layer, followed by distilling out materials having low boiling temperatures, which are mainly solvents used in the beginning of the reaction, to obtain a product.

Temperatures for distilling out the materials having low boiling temperatures are from 50° to 200° C., and preferably from 80° to 160° C.

When distilling out the materials, the degree of reduced pressure can be adjusted depending upon the boiling temperatures of the solvents to be used.

The reaction can be carried out by either a continuous type process or a batch type process.

In the case of the batch type process, starting materials and additives such as solvents, etc., are preferably charged firstly into a reaction vessel, and then an epoxidating agent is supplied dropwise.

When the reaction crude solution is washed with water after completion of the epoxidation reaction, the solution is separated into two liquid layers.

The organic liquid layer is separated from the water layer, followed by evaporation of low boiling components with an evaporator.

In the case of the continuous type process, starting materials, additives such as solvents and an epoxidating agent are supplied continuously into the reaction vessel, and the product is continuously taken out of the vessel.

The type of the reaction vessel includes a piston flow type or a completely mixable type vessel.

The product obtained is a composition mainly containing the compound represented by formula (II).

The constitution of the composition depends upon the constitution of the compound represented by formula (I), which is the starting material in the epoxidation reaction.

It appears that the composition obtained in the epoxidation reaction primarily contains compound of the formula (II), with the following various compounds in addition to the above described (I), (III), (VI), (VII), (VIII) and (IX).

$$Y^2-CO+O-(\underset{R^b}{\overset{R^a}{C}})_c-CO\overline{+_{n1}}O-CH_2-Y^2 \qquad (II)$$

$$Y^2-CO+O-(\underset{R^b}{\overset{R^a}{C}})_c-CO\overline{+_{n2}}O-CH_2-Y^1 \qquad (II)'$$

$$H+O-(\underset{R^b}{\overset{R^a}{C}})_c-CO\overline{+_{n3}}O-CH_2-Y^2 \qquad (VI)'$$

$$H+O-(\underset{R^b}{\overset{R^a}{C}})_c-CO\overline{+_{n4}}O-CH_2-Y^2 \qquad (VII)'$$

$$Y^2-CO-O-CH_2-Y^2 \qquad (III)'$$
$$Y^1-CO-O-CH_2-Y^2 \qquad (III)''$$

In formulae (II)', (VI)', (VII)', (III)', and (III)'', $Y^2$ represents at least one of the epoxidized structural groups

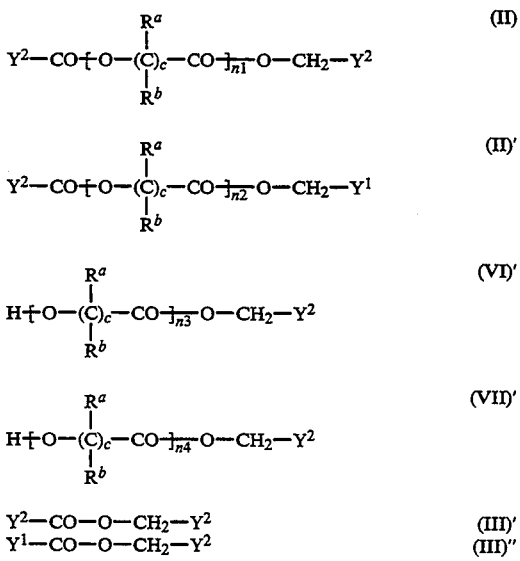

derived from the double bond in $Y^1$, and $Y^1$ and

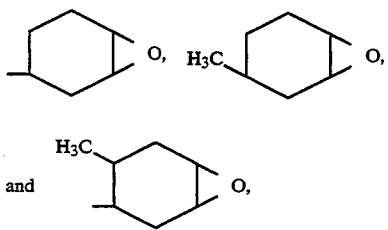

represent same structural groups as described hereinabove.

$R^a$, $R^b$ and c necessarily depend upon the lactone compound used, as well as in the compounds (I), (VI), (VII), (VIII) and (IX).

In the case that mixed lactones are used in an addition reaction of a lactone compound, the mixed lactone units are randomly introduced.

Accordingly, the epoxidized composition also inevitably is composed of various compounds having randomly introduced lactone units.

Also, n represents the same distributions as well as in the compounds (I), (VI), (VII), (VIII) and (IX).

Furthermore, it is noted that an epoxy group is generally ring-opened by water or an acid, even though present in a minor amount.

Accordingly, $Y^0$ is derived from $Y^2$ in compounds (II), (II)', (VI)', (VII)', and (III)' wherein $Y^0$ represents at least one of the structural groups

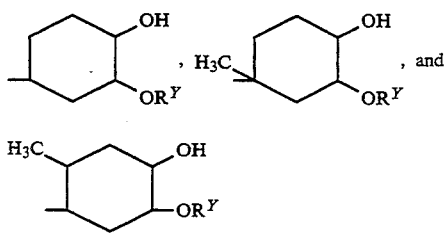

$R^Y$ represents hydrogen, acetyl group and or propyl group, etc., which depend upon the epoxidizing agent used.

The composition obtained by the epoxidation reaction, in which the compound of formula (II) is a main and desired component, can be used without any further treatments.

Furthermore, the composition can optionally be used after purifying, for example, with a chromatography, etc.

According to a fifth aspect of the present invention, there is provided a curable composition consisting essentially of the above described composition which comprises a compound represented by formula (II), and a curing agent for epoxy resins.

Specific curing agent includes an aromatic acid anhydride such as phthalic anhydride, trimellitic anhydride, pyromellitic anhydride, benzophenonetetracarboxylic anhydride, ethyleneglycol bis(anhydrotrimellitate), glyceroltris(anhydrotrimellitate), an alicyclic acid anhydride such as maleic anhydride, succinic anhydride, tetrahydrophthalic anhydride, methyltetrahydrophthalic anhydride, hexahydrophthalic anhydride, methylhexahydrophthalic anhydride, etc., and amines such as ethylenediamine, diethylenetriamine, triethylenetetramine, isophoronediamine, xylenediamine, methaphenylenediamine, diaminodimethyl sulfone, diaminodiphenyl methane, polymethylenediamine, etc., and/or imidazoles such as 2-methylimidazole, 2-ethyl-4-methylimidazole, 2-undecylimidazole, 2-heptadecylimidazole, 2-phenylimidazole, etc.

Furthermore, dicyandiamide and derivatives thereof, polyamide resins, an organic acid hydrazide, melamine and derivatives thereof, a trifluoroboric compound such as a trifluoroborate-amine complex, a compound having silanolic hydroxyl groups, etc., can be used as a curing agent for epoxy compounds.

Additionally, tertiary amines, esters of boric acid, Lewis acids, organometallic compounds, a salt of an organic acid, etc., can optionally be used together with the above described curing agents as an accelerator for curing.

Still further, a conventional modifier for epoxy resins and fillers can be used together with the curing agents.

The amount ratio of the curing agent to be used to the present epoxy composition is 1/0.1 to 1/5, preferably 1/0.5 to 1/1.5, based on the chemical equivalence, provided that a trifluoroborate-amine complex or a compound having silanolic hydroxyl groups are used in the chemical equivalence of from 1/0.0001 to 1/1.0, and preferably 1/0.001 to 1/1.0.

Furthermore, the alicyclic epoxy composition which comprises a compound represented by formula (II) can be used together with other epoxy resins in order to provide ductility to the other epoxy resins.

According to a sixth aspect of the present invention, there is provided a photo-polymerizable composition consisting essentially of the above described composition which comprises a compound represented by formula (II) and a photo-cationic polymerization initiator.

Specific photo-cationic polymerization initiator includes a diazonium salt such as

a sulfonium salt such as $R_3\text{-SMX}_m$ (XII),

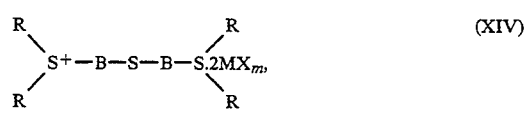

an iodonium salt such as $R-I^+-R.MX_m$ (XV), a metal complex such as

a sulfonium acetone such as

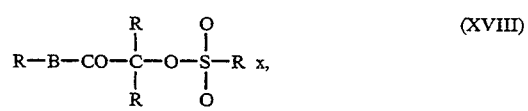

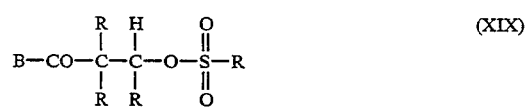

a sulfone compound such as

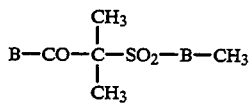

[in formulae (X) to (XX), B is

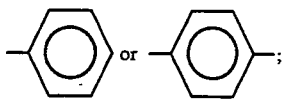

P is

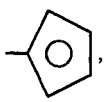

R is selected from hydrogen, an alkyl group, phenyl group, an aryl group and a hydroxyalkyl group, which may be identical or different from each other, $MX_m$ is at least one group selected from the group consisting of $SbF_6$, $AsF_6$, $PF_6$ and $BF_4$], a silicone compound having a property of generating a silanol group, or a complex of an aluminum compound by photo-irradiation.

The specific silicone compound is preferably a silicone compound having one group selected from the group consisting of a peroxysilane group, an o-nitrobenzyloxy group, and an alpha-ketosilyl group.

Specific silicone compounds having a peroxysilane group are represented by the formula $(R^{x1})_n$—Si(O—O—$R^{x2})_{4-n}$[in the formula, $R^{x1}$ and $R^{x2}$ hydrogen, a halogen atom, an alkyl group selected from the group consisting of, for example, methyl group, ethyl group, n-propyl group, isopropyl group, n-butyl group, t-butyl group, sec-butyl group, n-pentyl group, methoxy group, ethoxy group and chloromethyl group or an aryl group selected from the group of, for example, phenyl group, naphthyl group, anthranyl group, benzyl group, which may be identical or different from each other, and which can have a substituent selected from the group of a halogen atom, a nitro group, a cyano group, a methoxy group, etc., and n is a natural number of 0 to 3].

Silicone compounds have specific formulae are described hereinafter

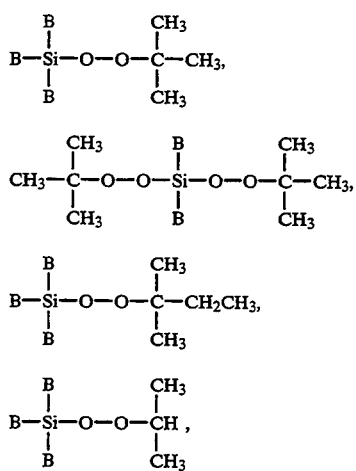

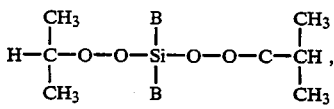

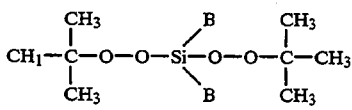

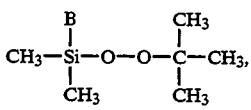

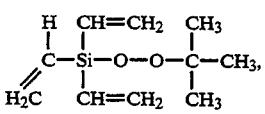

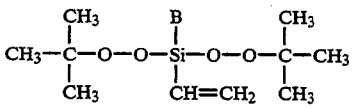

In the above formulae, B represents

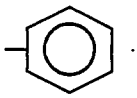

Specific silicone compounds having an o-nitrobenzyloxy group are described hereinafter.

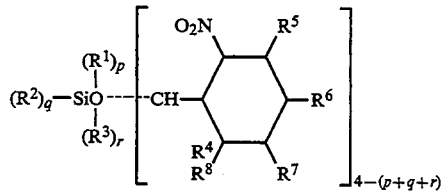

In the above formula, $R^1$, $R^2$ and $R^3$ are hydrogen, a halogen atom, vinyl group, an aryl group, a substituted or an unsubstituted alkyl group having a carbon number of from 1 to 10, an alkoxy group having a carbon number of from 1 to 10, a substituted or an unsubstituted aryl group, a substituted or an unsubstituted aryloxy group and or a siloxy group, respectively, which may be identical or different from each other; $R^4$ is hydrogen, a substituted or an unsubstituted alkyl group having a carbon number of from 1 to 10, or a substituted or an unsubstituted phenyl group; $R^5$, $R^6$, $R^7$ and $R^8$ are hydrogen, nitro group, cyano group, hydroxy group, mercapto group, a halogen atom, an acetyl group, an aryl group, an alkyl group having a carbon number of from 1 to 5, an alkoxy group having a carbon number of from 1 to 5, a substituted or an unsubstituted aryl group, a substituted or an unsubstituted aryl group and or an aryloxy group, respectively, which may be identical or different from each other; and p, q and r are each a natural number of 0 to 3, respectively, and have a relationship of $1 \leq p+q+r \leq 3$].

Substituted or unsubstituted alkyl groups having a carbon number of from 1 to 10 include methyl group, ethyl group, propyl group, n-butyl group, t-butyl group, pentyl group, chloromethyl group, chloroethyl group, fluoromethyl group and cyanomethyl group, etc., and specific alkoxy group having a carbon number of from 1 to 10 include a methoxy group, ethoxy group, n-propoxy group and or n-butoxy group, etc.

Substituted or unsubstituted aryl groups include a phenyl group, p-methoxyphenyl group, p-chlorophenyl group, p-trifluoromethylphenylvinylmethylphenyl(o-nitrobenzyloxy)silane, t-butylmethylphenyl(o-nitrobenzyloxy)silane, triethyl(o-nitrobenzyloxy)silane, tri(2-chloroethyl)-o-nitrobenzyloxysilane, tri(p-trifluoromethylphenyl)-o-nitrobenzyloxysilane, trimethyl[alpha-(o-nitrophenyl)-o-nitrobenzyloxy]silane, dimethylphenyl-[alpha-(o-nitrophenyl)-o-nitrobenzyloxy]silane, methylphenyldi[alpha-(o-nitrophenyl)-o-nitrobenzyloxy]silane, triphenyl(alpha-ethyl-o-nitrobenzyloxy)silane, trimethyl(3-methyl-2-nitrobenzyloxy)silane, dimethylphenyl(3,4,5-trimethoxy-2-nitrobenzyloxy)silane, triphenyl(4,5,6-trimethoxy-2-nitrobenzyloxy)silane, diphenylmethyl(5-methyl-4-methoxy-2-nitrobenzyloxy)silane, triphenyl(4,5-dimethyl-2-nitrobenzyloxy)silane, vinylmethylphenyl(4,5-dichloro-2-nitrobenzyloxy)silane, triphenyl(2,6-dinitrobenzyloxy)silane, diphenylmethyl(2,4-nitrobenzyloxy)silane, triphenyl(3-methoxy-2-nitrobenzyloxy)silane, vinylmethylphenyl(3,4-dimethoxy-2-nitrobenzyloxy)silane, dimethyldi(o-nitrobenzyloxy)silane, methylphenyldi(o-nitrobenzyloxy)silane, vinylphenyldi(o-nitrobenzyloxy)silane, t-butylphenyldi(o-nitrobenzyloxy)silane, diethyldi(o-nitrobenzyloxy)silane, 2-chloroethylphenyldi(o-nitrobenzyloxy)silane, diphenyldi(o-nitrobenzyloxy)silane, diphenyldi(3-methoxy-2-nitrobenzyloxy)silane, diphenyldi(3,4-dimethoxy-2-nitrobenzyloxy)silane, diphenyldi(2,6-dinitrobenzyloxy)silane, diphenyldi(2,4-dinitrobenzyloxy)silane, methyltri(o-nitrobenzyloxy)silane, phenyltri(o-nitrobenzyloxy)silane, p-bis(o-nitrobenzyloxydimethylsilyl)benzene, 1,1,3,3-tetraphenyl-1,3-di(o-nitrobenzyloxy)siloxane, and 1,1,3,3,5,5-hexaphenyl-1,5-di(o-nitrobenzyloxy)siloxane.

Furthermore, a silicone compound can be used, such as a silicone compound produced by a reaction between a SiCL-containing silicone resin and o-nitrobenzyl alcohol, a silicone compound having an alpha-ketosilyl group which is represented by the following formula;

$$(R^9)_L \diagdown$$
$$(R^{10})_m - Si-(CO-R^{12})_{4-(L+m+n)}$$
$$(R^{11})_n \diagup$$

(wherein L, m and n are each a natural number of 0 to 3, respectively; L+m+n is 3 or less than 3; $R^9$, $R^{10}$ and $R^{11}$ represent a hydrocarbon group such as an alkyl group having a carbon number of 1 to 10, an aryl group, an allyl group, vinyl group, an allyloxy group and an alkoxy group having a carbon number of 1 to 10, respectively, which can have a substituent such as a halogen atom, nitro group, cyano group and or methoxy group, which substituents may be identical or different from each other).

Specific compounds having an alpha-ketosilyl group include

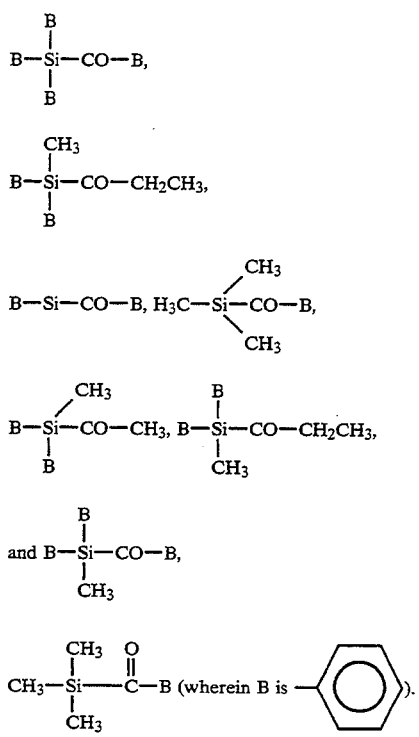

The mixing amount of the above described silicone compound is generally from 0.2 to 20% by weight, and preferably from 1 to 10% by weight, based on the weight of epoxy resin.

Where the amount is smaller than 0.1% by weight, curing of the epoxy resin is not sufficient.

On the other hand, where the amount is larger than 20% by weight, although available, it is not preferable because of costs and a problem caused by compounds derived from decomposition of the catalyst.

Furthermore, an aluminum compound can also be used as a photo-cationic polymerization initiator for the present epoxy compositions.

Specific aluminum compound includes trismethoxy aluminum, trisethoxy aluminum, trisisopropoxy aluminum, trisphenoxy aluminum, trisparamethylphenoxy aluminum, isopropoxy diethoxyaluminum, trisbutoxy aluminum, trisacetoxy aluminum, trisstearato aluminum, trisbutylate aluminum, trispropionato aluminum, trisisopropionato aluminum, trisacetylacetonato aluminum, tristrifluoroacetylacetonato aluminum, trishexafluoroacetylacetonato aluminum, trisethylacetonato aluminum, trissalicylaldehydato aluminum, trisdiethylmalolato aluminum, trispropylacetoacetato aluminum, trisbutylacetoacetato aluminum, trisdipivaloylmethanato aluminum, diacetylacetonatodipivaloylmethanato aluminum.

The above described compounds are represented by formulae

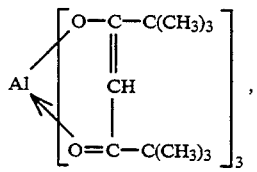

-continued

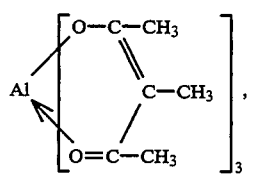

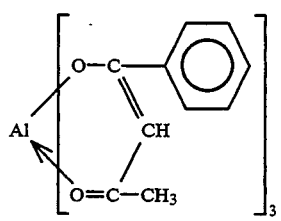

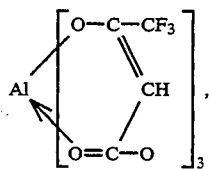

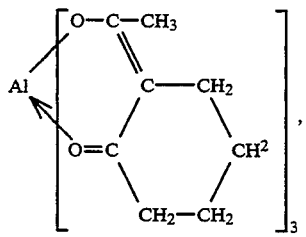

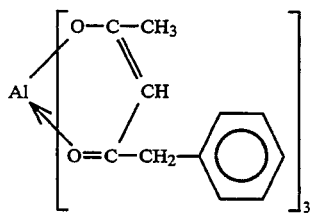

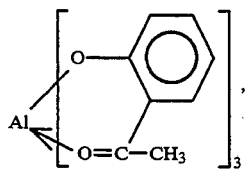

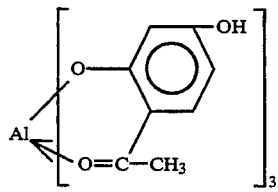

-continued

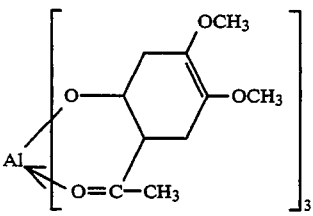

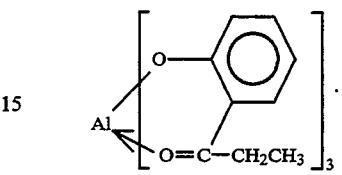

At least one of the above described aluminum compounds can be used, in a general amount of from 0.001 to 10% by weight, and preferably from 1 to 5% by weight, based on the weight of epoxy composition.

Where the amount is less than 0.001% by weight, sufficient properties, for example, tensile strength or tensile elongation, etc., can not be attained in the cured products.

On the other hand, where the amount is larger than 10% by weight, it is not preferable because of costs and a problem of a tendency of lowering of resistance of moisture.

Various anti-staining agents can be mixed in the present photo-polymerizable composition for the purpose of increasing a resistance to staining. Specific anti-staining agents include borates, phosphates, chromates, molybdenum salts, etc.

The anti-staining agents can be generally used in an amount of from 10 to 50% by weight, based on the weight of epoxy composition.

Furthermore, various additives such as coloring dyes or pigments, a silica, an alumina can also be used together therewith.

From the viewpoint of practical use, the present photo-polymerizable composition can be coated on a base material, and cured by photo-curing at ordinary temperatures (e.g., 25° C.), or by photo-curing during heating, and postcuring after the photo-curing.

Although the wavelength of rays to be irradiated for photo-curing depends upon a mixing constituent of the present photo-polymerizable composition and the kind of the above described photo-initiator, it is usually from 180 to 700 nm, and preferably in the ultraviolet wavelength range.

The irradiation period of time also depends upon the mixing constituents of the photo-polymerizable composition, the kind of the above described photo-initiator, and the kind of the irradiation source. Generally, it is from 10 seconds to 30 minutes, and preferably, it is from 20 to 60 seconds.

Furthermore, the temperature for photo-curing during heating also depends upon the mixing constituent of the photo-polymerizable composition, and the kind of the above described photo-initiator; it is usually from 20° to 200° C., and preferably, is from 60° to 100° C.

Still further, the temperature for postcuring after the photo-curing also depends upon the mixing constituents of the present photo-polymerizable composition, and the kind of the above described photo-initiator; it is usually from 50° to 200° C., and preferably is from 100° to 180° C.

There can be used a low-voltage mercury lamp, a high-voltage mercury lamp, a carbon arc lamp, a xenon lamp, an argon glow discharge lamp, a metal halide lamp, etc., as a discharging source of irradiation rays.

The following Examples are given to illustrate the practice of this invention but they are not intended in any way to act to limit the scope of this invention.

EXAMPLE 1

A reaction vessel having a capacity of 3 litters equipped with a mechanically-driven stirrer, a reflux condenser, and a thermometer was charged with 1211.7 g. of 1,2,5,6-tetrahydrobenzyl-1,2,5,6-tetrahydrobenzoate (above described compound (III)), 626.9 g. of epsilon-caprolactone, 8.51 g. of diethylene glycol, and 9.20 g. of 1% heptane solution of tetrabutyltitanate as a catalyst.

The contents in the vessel were gradually raised to a temperature of 220° C., followed by heating for 27 hours, under the presence of a nitrogen gas stream, to obtain an epsilon-caprolactone adduct.

peaks were observed at 3020 cm$^{-1}$, 1659 cm$^{-1}$ and 647 cm$^{-1}$, which are derived from specific double bonds of cyclohexenyl group.

It was confirmed that the esterification reaction as described hereinabove occurred by the presence of a molecular weight distribution in the GPC chart.

It was confirmed by the above analyses that the product is represented by formula described hereinafter.

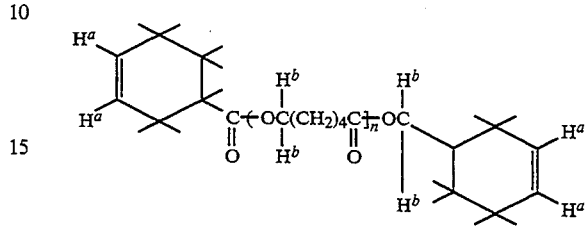

(wherein n=0, 1, 2, 3, 4 . . . ).

The mixing constituents of reaction materials and the results obtained in further Examples 2–9 are shown below in Table 1.

TABLE 1

| Example | Compound (III) | E.C. | DEG | TBT | Reaction Temperature (°C.) | Reaction Time (hour) | Residual component (wt %) Compound (III) | Residual component (wt %) E.C. | Outer appearance (APHA) | Acid value | Hydroxyl value | H$_2$O (%) | Viscosity (cp/45° C.) |
|---|---|---|---|---|---|---|---|---|---|---|---|---|---|
| 1 | 1211.7 | 626.9 | 8.51 | 9.20 | 220 | 27 | 30.17 | 0.16 | 80 | 0.33 | 5.00 | 0.010 | 45 |
| 2 | 749 | 116.3 | 9.0 | 9.65 | 220 | 27 | 10.37 | 0.24 | 100 | 0.45 | 4.95 | 0.010 | 92 |
| 3 | 550.7 | 1426.7 | 9.5 | 9.70 | 220 | 26 | 4.66 | 0.26 | 90 | 0.66 | 4.95 | 0.013 | 148 |
| 4 | 1233.7 | 639.2 | 26.6 | 9.50 | 220 | 30 | 32.33 | 0.20 | 100 | 0.30 | 15.00 | 0.013 | 40 |
| 5 | 220.7 | 571.6 | 2.0 | 4.10 | 220 | 32 | 4.95 | 0.21 | 80 | 0.45 | 0.28 | 0.011 | 153 |
| 6 | 220.7 | 571.6 | 11.9 | 4.00 | 220 | 17 | 4.29 | 0.34 | 90 | 1.34 | 15.93 | 0.010 | 141 |
| 7 | 100.0 | 261.5 | 50.7 | 0.4 | 220 | 27 | 3.42 | 0.46 | 100 | 0.50 | 129.0 | 0.010 | 120 |
| 8 | 222.9 | 580.4 | 112.7 | 4.56 | 220 | 10 | 2.98 | 0.58 | 110 | 0.14 | 126.04 | 0.011 | 136 |
| 9 | 682.3 | 353.5 | 5.1 | 5.30 | 220 | 30 | 55.81 | 0.13 | 100 | 0.49 | 5.02 | 0.010 | 23 |

E.C.: epsilon-caprolactone
DEG: diethyleneglycol
TBT: tetrabutyltitanate (addition in the form of 1% heptane solution)
Acid value: KOH mg/g
Hydroxyl value: KOH mg/g It was confirmed by gas chromatography analysis that 30.17% of 1,2,5,6-tetrahydrobenzyl-1,2,5,6-tetrahydrobenzoate and 0.16% of unreacted epsilon-caprolactone remained in the epsilon-caprolactone adduct.

The lactone adduct having double bonds exhibited the properties, an outer appearance(APHA), an acid value(mg KOH/g), a hydroxyl value(mg KOH/g), a viscosity value(cp/45° C.) and water content (%) as shown in Table 1. Successively, the adduct was analyzed with a $^1$H-NMR, an I.R. spectrometer, and GPC (gel permeation chromatography).

Figure 2:
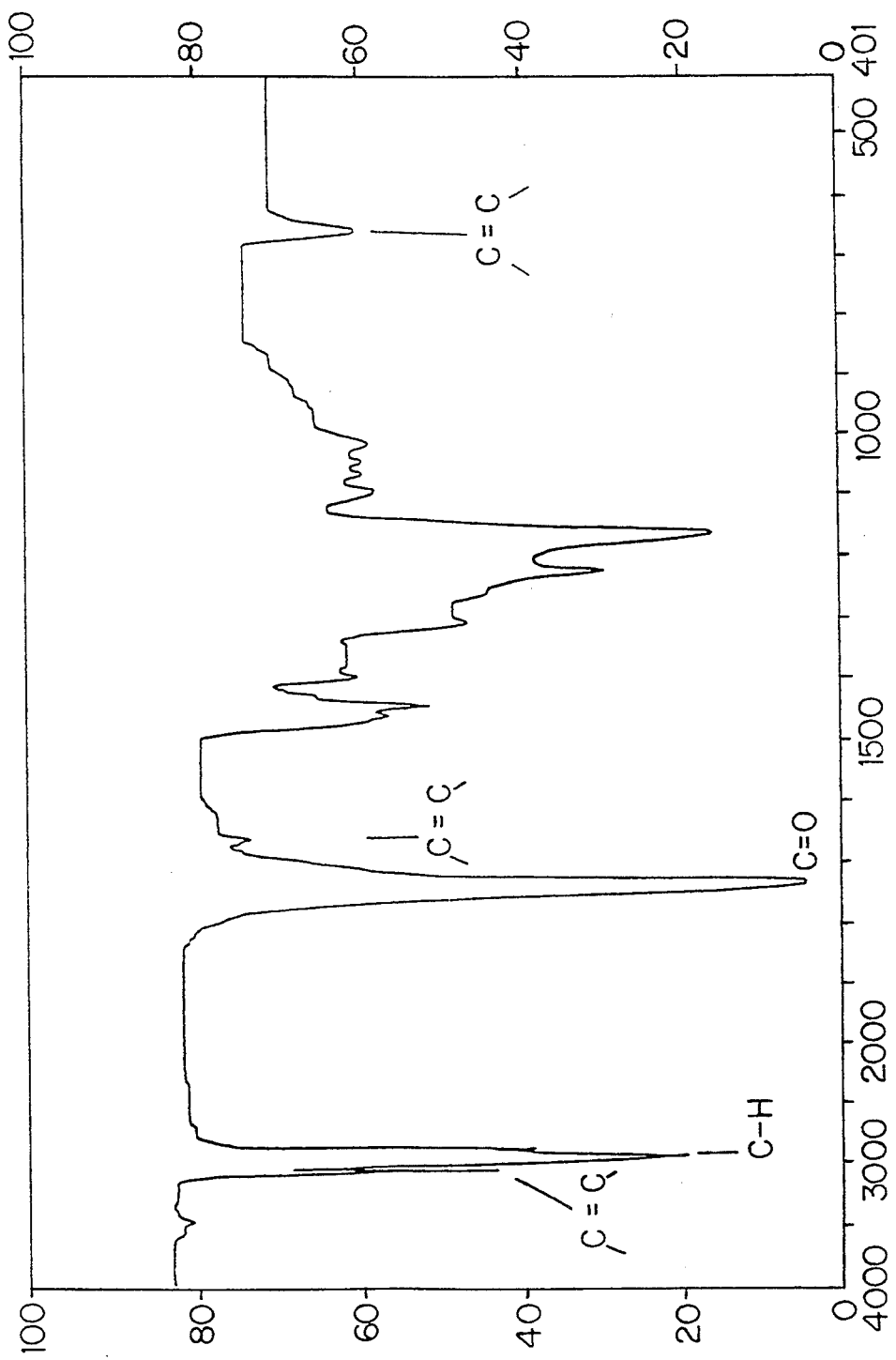
FIG. 2 is an IR(Infra-Red) spectrum chart.
Figure 3:
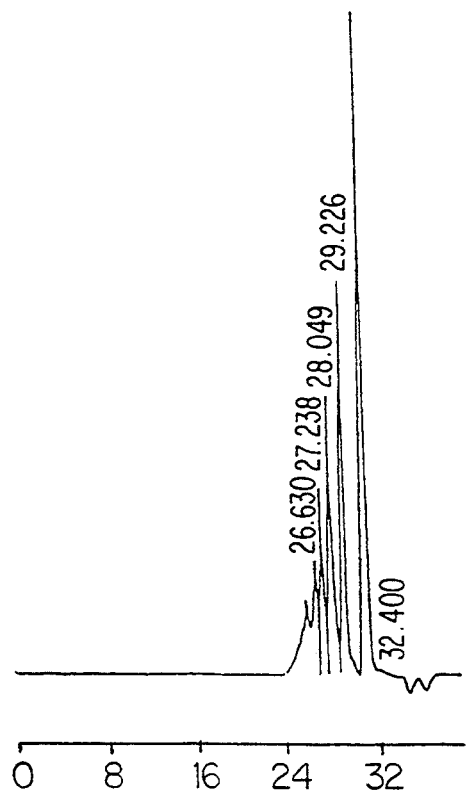
FIG. 3 is a GPC(Gel Permeation Chromatography) chart relating to the composition obtained in Example 1, respectively.

These spectra are illustrated in FIG. 1, FIG. 2, and FIG. 3, respectively.

The $^1$H-NMR spectrum chart was obtained with CDCL$_3$ as a solvent, under room temperatures, by using a JNM-EX 90 apparatus (manufactured by Nihon Denshi, Ltd.).

In the NMR spectrum chart, a singlet delta 5.67(H$^a$) is derived from a hydrogen bonded to a carbon atom having double bonds, and a multiplet delta 3.9 to 4.2(H$^b$,H$^b$) belongs to a hydrogen of methylene group which is adjacent to an oxygen atom.

The I.R. spectrum chart was obtained by using an IR-435 spectrometer (manufactured by Shimadzu Seisakusyo, Ltd.), and an NaCL plate on which a sample was coated.

An absorption peak was observed at 1728 cm$^{-1}$, which is derived from carbonyl group, and absorption

EXAMPLE 10

A reaction vessel having a capacity of 2 liters equipped with a mechanically-driven stirrer, a reflux condenser, a thermometer, and a muffle was charged with 167.2 g. of the composition containing the compound (I) obtained in Example 1, 150.0 g. of ethyl acetate.

The contents in the vessel were maintained at a temperature of 50° C.

Successively, peracetic acid solution (concentration of 30% in ethyl acetate) and 1.48 g. of 2-ethylhexyl sodium tripolyphosphate were charged by dropwise addition into the contents over 2 hours.

The contents were further maintained at a temperature of 50° C. for 2 hours, to obtain a crude reaction solution having acetic acid concentration of less than 0.1%.

320 g. of ion-exchanged water was added into the crude reaction solution obtained, followed by stirring at a temperature of 50° C. for 30 minutes.

The solution was aged for approximately 40 minutes to separate into two liquid layers. The lower layer liquid was gradually removed from the upper layer liquid over 20 minutes.

150 mL of ethyl acetate was added into the separated upper layer liquid. The same addition processes of ion-exchanged water and separation were further repeated twice.

Low boiling components in the upper layer liquid obtained were removed with a Smith-type thin layer evaporator made of glass.

Operating conditions of the evaporator were a heating temperature of 150° C. and a reduced pressure of 10 mm Hg.

Yield of the epoxidized compound represented by formula (II) was 95% based on the amount of the upper layer liquid after removing the low boiling components. The properties of the compound are shown in Table 2.

The $^1$-NMR spectrum chart was obtained with CDCL$_3$ as a solvent, under room temperatures by using a JNM-EX 90 apparatus (manufactured by Nihon Den-

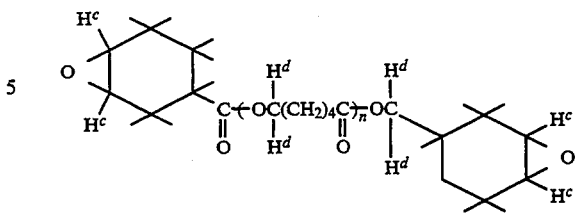

(wherein n=approximately 10).

The mixing constituents of reaction materials and the results obtained in further Examples 11–15 are shown below in Table 2.

TABLE 2

| Example | Compound obtained in each Example | EA (g) | AP (g) | 2E | RT (°C.) | APDT (hour) | AGT (hour) | color (APHA) | AV | H$_2$O (%) | Viscosity (cp/45° C.) | OX (%) | Y (%) |
|---|---|---|---|---|---|---|---|---|---|---|---|---|---|
| 10 | Ex. 1 | 167.2 | 150.0 | 275.5 | 1.48 | 50 | 2 | 2 | 30 | 0.90 | 0.009 | 214 | 6.96 | 95 |
| 11 | Ex. 2 | 187.6 | 166.7 | 185.6 | 1.08 | 50 | 2.5 | 1.5 | 65 | 0.98 | 0.007 | 274 | 4.57 | 95 |
| 12 | Ex. 3 | 263.7 | 250.0 | 194.9 | 1.44 | 50 | 3 | 2 | 70 | 0.83 | 0.007 | 340 | 3.73 | 94 |
| 13 | Ex. 5 | 197.7 | 175.7 | 144.4 | 1.06 | 50 | 2.5 | 1.5 | 70 | 1.31 | 0.009 | 353 | 3.38 | 96 |
| 14 | Ex. 6 | 200.0 | 200.0 | 168.4 | 1.17 | 50 | 2 | 2 | 65 | 0.827 | 0.005 | 338 | 3.42 | 97 |
| 15 | Ex. 8 | 197.7 | 175.7 | 144.4 | 1.03 | 50 | 2.5 | 2 | 70 | 1.25 | 0.050 | 347 | 2.73 | 95 |
| 18 | Ex. 16 | 167.0 | 150.0 | 275.5 | 1.48 | 50 | 2.0 | 2.0 | 50 | 1.80 | 0.01 | 110 | 7.20 | 91 |
| 19 | Ex. 17 | 167.0 | 150.0 | 275.5 | 1.48 | 50 | 2.0 | 2.0 | 50 | 0.70 | 0.05 | 100 | 7.19 | 91 |
| C.E. 1 | Ex. 1 | 167.2 | 150.0 | 275.5 | 1.48 | 50 | 2 | 2 | — | 2.8 | 0.009 | 214 | 7.0 | 95 |

C.E. 1: Comparative Example 1.
EA: Ethyl acetate
AP: Acetic peracid
2E: 20% 2-ethylhexylsodiumtriphosphate solution
RT: Reaction temperature
APDT: Dropwise addition time of Acetic peracid
AGT: Aging time
AV: Acid value (KOH mg/g)
OX: Oxyrane oxygen
Y: Yield shi, Ltd.).

In the $^1$H-NMR spectrum chart, it was confirmed that a peak at delta 5.6 derived from a double bond in the raw material shifts to delta (ppm)3.-2(H$^c$) which is a higher magnetic field, by the epoxidation of the double bonds. It was confirmed that a double bond was epoxidized by the NMR data.

Figure 4:
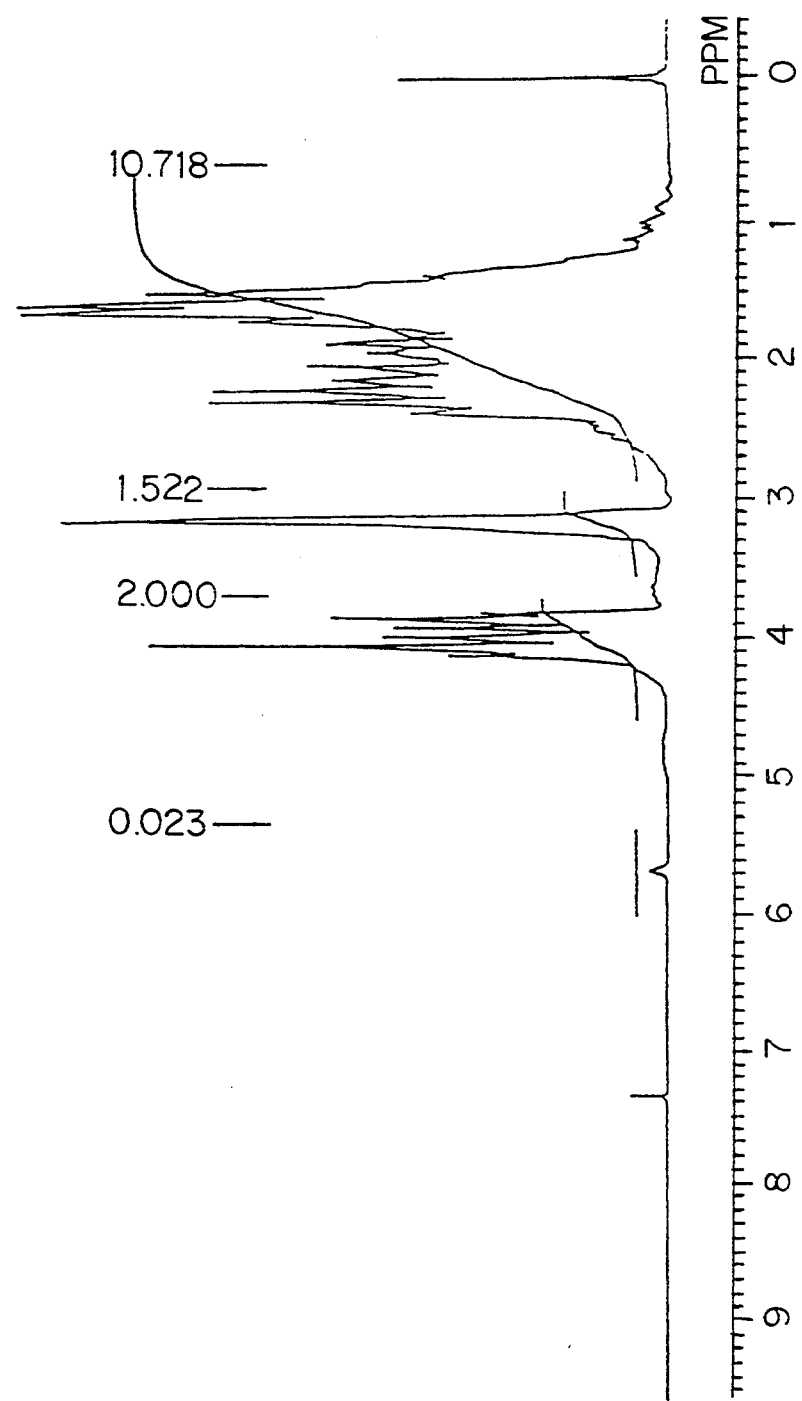
FIG. 4 is a $^1$H-NMR chart and FIG. 5 is an IR spectrum chart relating to the composition obtained in Example 10, respectively.

Furthermore, in the NMR spectrum chart, a multiplet delta 3.8 to 4.2(H$^d$,H$^{d'}$) belongs to a hydrogen of methylene group which is adjacent to an oxygen atom (as shown in FIG. 4).

Figure 5:
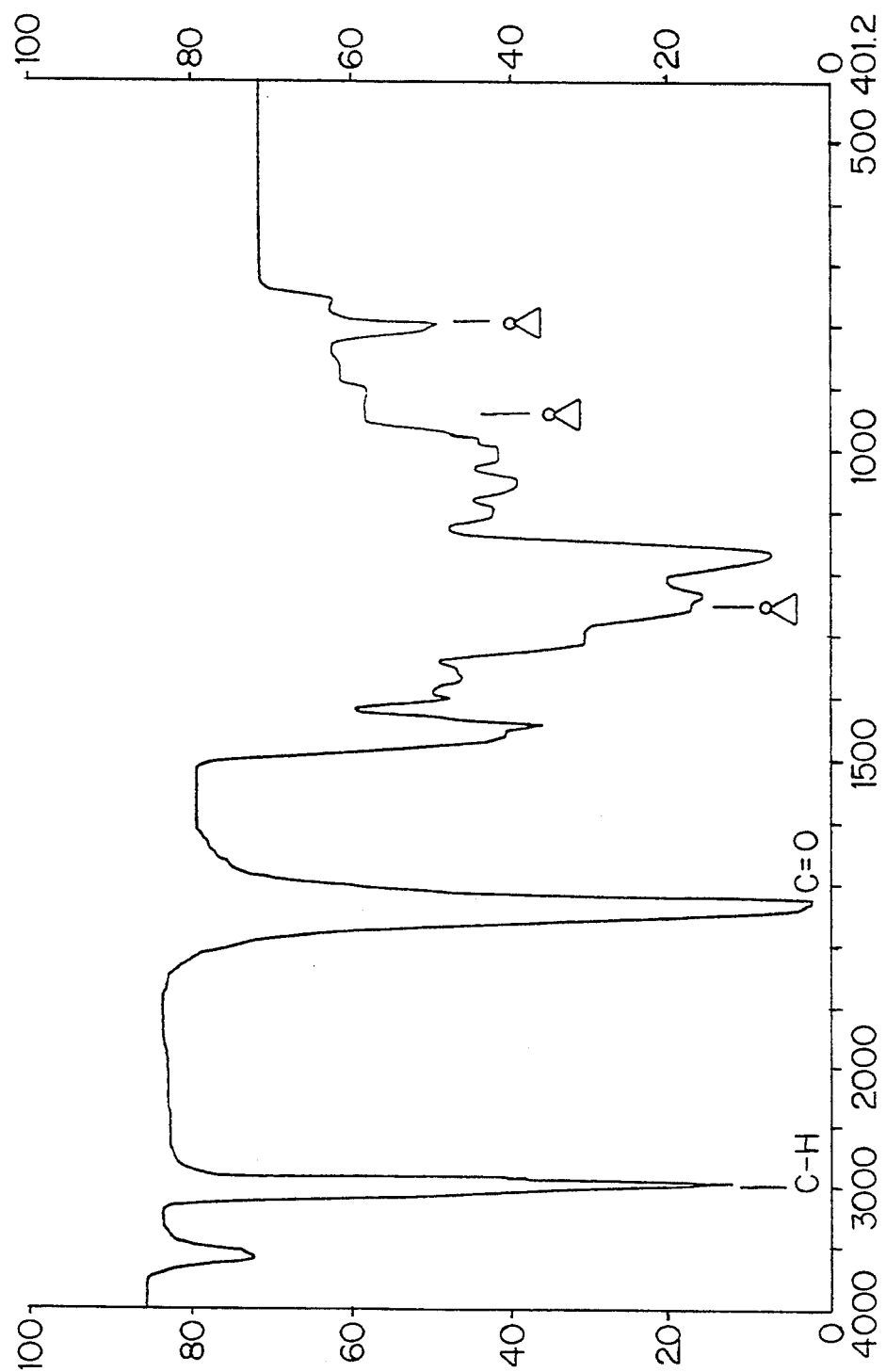

An absorption peak in IR spectrum was observed at 1734 cm$^{-1}$, which is derived from carbonyl group, and absorption peaks were observed at 785 cm$^{-1}$, 1250 cm$^{-1}$, which are especially derived from an epoxy group, as shown in FIG. 5.

The I.R. spectrum chart was obtained by using IR-435 spectrometer (manufactured by Shimadzu Seisakusyo, Ltd.), and NaCL plate on which a sample was coated.

It was confirmed that the obtained epoxy compound is represented by the rational formula described hereinafter by the above analyses;

EXAMPLE 16

A reaction vessel having a capacity of 3 liters equipped with a mechanically-driven stirrer, a reflux condenser, and a thermometer was charged with 1211.0 g. of 1,2,5,6-tetrahydrobenzyl-1,2,5,6-tetrahydrobenzoate [compound (III)], 300.0 g. of epsilon-caprolactone, 326 g. of beta-methyldeltavalerolactone, 8.51 g. of diethyleneglycol, and 9.20 g. of 1% heptane solution of tetrabutyltitanate as a catalyst.

The contents in the vessel were gradually raised to a temperature of 220° C., followed by heating for 27 hours, under the presence of a nitrogen gas stream, to obtain a mixed-lactone adduct.

It was confirmed by gas chromatography analysis that 30.0% of 1,2,5,6-tetrahydrobenzyl-1,2,5,6-tetrahydrobenzoate (compound (III)), 0.01% of unreacted epsilon-caprolactone, and 3.0% of beta-methyldeltavalerolactone remained in the mixed lactone adduct.

The mixed-lactone adduct having double bonds exhibited the following properties; an outer appearance(APHA) of 100, an acid value(mg KOH/g) of 0.1, a hydroxyl value(mg KOH/g) of 4.86, and a water content of 0.01%.

EXAMPLE 17

A reaction vessel having a capacity of 3 liters equipped with a mechanically-driven stirrer, a reflux condenser, and a thermometer was charged with 1211.0 g. of 1,2,5,6-tetrahydrobenzyl-1,2,5,6-tetrahydrobenzoate (compound (III)), 300.0 g. of epsilon-caprolactone, 326 g. of trimethylcaprolactone(a mixture composed of 3,5,5-trimethylcaprolactone and 3,3,5-trimethylcaprolactone), 8.51 g. of diethyleneglycol, and 9.20 g. of 1% heptane solution of tetrabutyltitanate as a catalyst.

The contents in the vessel were gradually raised to a temperature of 220° C., followed by heating for 27 hours under the presence of a nitrogen gas stream to obtain a mixed-lactone adduct.

It was confirmed by gas chromatography analysis that 31.0% of 1,2,5,6-tetrahydrobenzyl-1,2,5,6-tetrahydrobenzoate (compound (III)) 0.10% of unreacted epsilon-caprolactone, and 3.0% of trimethylcaprolactone remained in the mixed-lactone adduct.

The obtained mixed-lactone adduct exhibited the following properties; an outer appearance(APHA) of 1000, an acid value(mg KOH/g) of 0.1, a hydroxyl value(mg KOH/g) of 4.86, and water content of 0.01%.

EXAMPLE 18 AND EXAMPLE 19

The same procedures described in Example 10 were repeated, except that the product obtained in Example 16 and the product obtained in Example 17 were used, respectively.

The results obtained in Examples 18 and 19 are also shown in Table 2.

Comparative Example 1

The same procedures described in Example 10 were repeated, except that 2-ethylhexylsodiumtripolyphosphate was not used.

The product obtained exhibited a high acid value of 2.8.

EXAMPLE 20

A reaction vessel equipped with a tube for supplying nitrogen gas, a funnel for dropwise addition, a mechanically-driven stirrer, a reflux condenser, a thermometer was charged with 440 parts by weight of 1,2,5,6-tetrahydrobenzyl-1,2,5,6-tetrahydrobenzoate[a compound represented by formula (III)], 228 parts by weight of epsilon-caprolactone, 2.9 parts by weight of diethyleneglycol and 3.1 parts by weight of heptane solution containing 3% of tetrabutyltitanate as a catalyst.

The contents in the vessel were heated to approximately 220° C. under a nitrogen gas stream for approximately 1 hour, and allowed to react to obtain 668 parts by weight of a lactone adduct [a composition comprising a compound represented by formula(I)] for 27 hours.

Unreacted 1,2,5,6-tetrahydrobenzyl-1,2,5,6-tetrahydrobenzoate and epsilon-caprolactone were present in the lactone adduct product in amounts of 30.2% by weight and 0.16% by weight, respectively.

The lactone adduct obtained exhibited an acid value of 0.33, a hydroxyl value of 5.0, and a viscosity of 45 cp/45° C.

A reaction vessel equipped with a tube for supplying nitrogen gas, a funnel for dropwise addition, a mechanically-driven stirrer, a muffle, a thermometer, and a reflux condenser was charged with 500 parts by weight of the lactone adduct, and 450 parts by weight of ethyl acetate, followed by heating to a temperature of 50° C.

Successively, 800 parts by weight of ethyl acetate solution containing 30% of peracetic acid, and 1.5 parts by weight of 2-ethylhexyl sodium tripolyphosphate, were added dropwise into the ethyl acetate solution of the above lactone adduct for 2 hours, and the contents in the reaction vessel were maintained for additional reaction at 50° C. for 2 hours.

The concentration of peracetic acid was less than 0.6% after the additional reaction.

Successively, 960 parts by weight of ion-e changed water were added into the crude reaction solution obtained to wash and to separate it into two liquid layers.

The lower liquid layer was removed from the upper liquid layer.

450 parts by weight of ion-exchanged water were added into the upper layer to again wash it. The same addition processes of ion-exchange water were repeated twice further.

Low boiling components were removed from the upper layer liquid obtained at a temperature of 150° C. and a reduced pressure of 10 mm Hg to obtain 520 parts by weight of a composition comprising a compound represented by formula (II) (epsilon-caprolactone modified 3,4-epoxycyclohexylmethyl-3',4'-epoxycyclohexanecarboxylate).

It is noted that a specific example of 3,4-epoxycyclohexylmethyl-3',4'-epoxycyclohexanecarboxylate is Celloxide 2021, manufactured by Daicel Chemical Industries, Ltd., corresponding to the compound represented by formula (IV) having a residual group of cyclohexenemonoepoxide, that is,

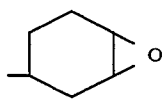

as $Y^2$.

The epoxidized lactone adduct exhibited an epoxy equivalence of 230, an acid value of 0.90, and a viscosity of 214 cp/45° C.

The epoxidized lactone adduct was designated as Epoxy Resin A.

EXAMPLE 21

The same procedures as described in Example 20 were repeated, except that 342 parts by weight of epsilon-caprolactone were added to 252 parts by weight of 1,2,5,6-tetrahydrobenzyl-1,2,5,6-tetrahydrobenzoate to obtain a lactone adduct, and the lactone adduct was epoxidised.

The epoxidized lactone adduct was designated as Epoxy Resin B.

EXAMPLE 22

The same procedures as described in Example 20 were repeated, except that 570 parts by weight of epsilon-caprolactone were added to 252 parts by weight of 1,2,5,6-tetrahydrobenzyl-1,2,5,6-tetrahydrobenzoate to obtain a lactone adduct, and the lactone adduct was epoxidised.

The epoxidized lactone adduct was designated as Epoxy Resin C.

EXAMPLE 23

The same procedures as described in Example 20 were repeated, except that 468 parts by weight of trimethylcaprolactone were added to 280 parts by weight of 6-methyl-1,2,5,6-tetrahydrobenzyl-6-methyl-1,2,5,6-tetrahydrobenzoate to obtain a lactone adduct, and the lactone adduct was epoxidised.

The epoxidized lactone adduct was designated as Epoxy Resin D.

Application Example 1

100 parts by weight of the Epoxy Resin A, 82 parts by weight of methylhexahydrophthalic anhydride as a curing agent and 0.91 parts by weight of N,N'-dimethylbenzyl amine as a catalyst were mixed in a vessel at room temperature, followed by being cured at the temperature of 100° C. for 5 hours to obtain a cured product.

The cured product was further cured at the temperature of 160° C. for 10 hours to obtain a cured product for tests.

Application Example 2

100 parts by weight of the Epoxy Resin B, 42 parts by weight of hexahydrophthalic anhydride as a curing agent and 0.74 parts by weight of N,N'-dimethylbenzyl amine as a catalyst were mixed and cured as described in Application Example 1 to obtain a cured product for tests.

Application Example 3

100 parts by weight of the Epoxy Resin C, 34 parts by weight of methylhexahydrophthalic anhydride as a curing agent and 0.67 parts by weight of N,N'-dimethylbenzyl amine as a catalyst were mixed and cured as described in Application Example 1 to obtain a cured product for tests.

Application Example 4

45 parts by weight of the Epoxy Resin C, 55 parts by weight of 3,4-epoxycyclohexylmethyl-3',4'-epoxycyclohexanecarboxylate, 66 parts by weight of phthalic anhydride as a curing agent and 0.83 parts by weight of N,N'-dimethylbenzyl amine as a catalyst were mixed and cured as described in Application Example 1 to obtain a cured product for tests.

Application Example 5

100 parts by weight of the Epoxy Resin D, 30 parts by weight of methylhexahydrophthalic anhydride as a curing agent and 0.65 parts by weight of N,N'-dimethylbenzyl amine as a catalyst were mixed and cured as described in Application Example 1 to obtain a cured product for tests.

Comparative Application Example 1

The same procedures as described in Application Example 1 were repeated, except that 100 parts by weight of 3,4-epoxycyclohexylmethyl- 3',4'-epoxycyclohexanecarboxylate [Celloxide 2021 manufactured by Daicel Chemical Industries, Ltd.], 114 parts by weight of methylhexahydrophthalic anhydride and 1.07 parts by weight of N,N-dimethylbenzylamine as a curing agent were mixed.

Comparative Application Example 2

The same procedures as described in Application Example 1 were repeated, except that 31 parts by weight of 3,4-epoxycyclohexylmethyl-32',4'-epoxycyclohexanecarboxylate [Celloxide 2021 manufactured by Daicel chemical Industries, Ltd.], 69 parts by weight of a polycaprolactone polyol (PCL-305 manufactured by Daicel Chemical Industries, Ltd.), 38 parts by weight of methylhexahydrophthalic anhydride and 0.69 parts by weight of N,N-dimethylbenzylamine as a curing agent were mixed.

Comparative Application Example 3

The same procedures as described in Application Example 1 were repeated, except that 100 parts by weight of bis(3,4-epoxycyclohexylmethyl)adipate [ERL-4299 manufactured by Union Carbide, Corp.], 81 parts by weight of methylhexahydrophthalic anhydride and 0.91 parts by weight of N,N-dimethylbenzylamine as a curing agent were mixed.

The mixing constituents and various properties obtained in Application Examples 1 to 5 and Comparative Application Examples 1 to 3 are shown in Table 3 and Table 4, respectively.

TABLE 3

|  | Application Example | | | | | Comparative Application Example | | |
|---|---|---|---|---|---|---|---|---|
|  | 1 | 2 | 3 | 4 | 5 | 1 | 2 | 3 |
| Epoxy Resin A | 100 | | | | | | | |
| Epoxy Resin B | | 100 | | | | | | |
| Epoxy Resin C | | | 100 | 45 | | | | |
| Epxoy Resin D | | | | | 100 | | | |
| Celloxide 2021(*1) | | | | 55 | | 100 | 31 | |
| ERL-4229(*2) | | | | | | | | 100 |
| PCL-305(*3) | | | | | | | 69 | |
| metyl hexahydrophthalic anhydride | 82 | | 34 | | 30 | 114 | 38 | 81 |
| hexahydrophthalic anhydride | | 42 | | | | | | |
| phthalic anhydride | | | | 66 | | | | |
| N,N'-dimethylbenzylamine | 0.91 | 0.74 | 0.67 | 0.83 | 0.65 | 1.07 | 0.69 | 0.91 |

Note:
Celloxide 2021: 3,4-epoxycyrohexylmethyl-3',4'-epoxycyclohexanecarboxylate [manufactured by Daicel Chemical Industries, Ltd.]
ERL-4229: bis(3,4-epoxycyrohexylmethyl)adipate [manufactured by Union Carbide Corp.]
PCL-305: polycaprolactonetriol [manufactured by Daicel Chemical Industries, Ltd.]

TABLE 4

|  | Application Example | | | | | Comparative Application Example | | |
|---|---|---|---|---|---|---|---|---|
|  | 1 | 2 | 3 | 4 | 5 | 1 | 2 | 3 |
| Gel time of composition (min/100° C.) | 121 | 137 | 192 | 139 | 140 | 96 | — | 120 |
| Heat distortion Temperature (°C.) | 111 | 29 | ≦20 | 115 | 30 | 186 | ≦20 | 131 |
| Glass transition Temperature (°C.) | 116 | 5 | −23 | 120 | 7 | — | −7 | 132 |
| Tensile strength (kgf/mm2) | 6.9 | 1.8 | 0.3 | 6.0 | 1.8 | 4.3 | * | 6.2 |
| Tensile elongation (%) | 7 | 42 | 160 | 5 | 40 | 2 | * | 5 |
| Flexural strength (kgf/mm2) | 9.6 | — | — | — | — | 10.8 | * | 10.9 |
| Flexural elongation (%) | 140 | — | — | — | — | 4 | * | 93 |

TABLE 4-continued

| | Application Example | | | | | Comparative Application Example | | |
|---|---|---|---|---|---|---|---|---|
| | 1 | 2 | 3 | 4 | 5 | 1 | 2 | 3 |
| Izod Impact strength (kgf · cm/cm) | 0.62 | 5.5 | — | 1.6 | 5.4 | 1.2 | * | 0.47 |
| Water absorption (%) | 0.28 | 0.48 | 0.86 | 0.28 | 0.48 | 0.35 | * | 0.32 |

Note:
* Incapable of measuring because of no-curing

EXAMPLE 24

The same procedures as described in Example 20 were repeated, except that 3 mols of epsilon-caprolactone were added to 1 mol of 1,2,5,6-tetrahydrobenzyl-1,2,5,6-tetrahydrobenzoate to obtain an epoxidized lactone adduct. The epoxidized lactone adduct was designated as Epoxy Resin EP-1.

EXAMPLE 25

The same procedures as described in Example 20 were repeated, except that 2 mols of trimethylcaprolactone were added to 1 mol of 1,2,5,6-tetrahydrobenzyl-1,2,5,6-tetrahydrobenzoate to obtain an epoxidized lactone adduct. The epoxidized lactone adduct was designated as Epoxy Resin EP-2.

Application Example 6

100 parts by weight of the Epoxy Resin EP-1, 0.5 parts by weight of trisacetyl(acetonato)-aluminum and 3 parts by weight of triphenyl(o-nitrobenzyloxy)silane as a photo-cationic polymerization initiator were mixed and cured to obtain a photocured plate having a thickness of 2 mm under the illuminance of irradiation with a metalhalide lamp having 80 W/cm$_2$, with an exposing distance of 6.5 cm, for the period of time of 100 seconds.

Application Example 7

The same procedures as described in Application Example 6 were repeated, except that 100 parts by weight of the Epoxy Resin EP-2 and 1 part by weight of trisethyl(acetoacetato)-aluminum were used to obtain a photocured plate.

Comparative Application Example 4

The same procedures as described in Application Example 6 were repeated, except that 100 parts by weight of 3,4-epoxycyclohexylmethyl- 3',4'-epoxycyclohexanecarboxylate (Celloxide 2021, manufactured by Daicel Chemical Industries, Ltd.) were used to obtain a photocured plate.

Comparative Application Example 5

The same procedures as described in Application Example 6 were repeated, except that 100 parts by weight of Epikote 828 (an epi-bis type epoxy resin manufactured by Ciba-Geigy, Corp.) were used to obtain a photocured plate.

The measurements of the properties of the cured plates were carried out under the conditions of temperature of 20° C. and relative humidity of 65%. Measurements of the tensile strength and elongation were carried out based on JIS K 6911.

The measurements of Tg were carried out with a high performance differential calorimeter (No. DSC 8230B manufactured by Rigaku Denki, Ltd.).

The mixing constituents and various properties obtained in Application Examples 6, 7 and Comparative Application Examples 4, 5 are shown in Table 5.

TABLE 5

| | Application Example | | Comparative Application Example | |
|---|---|---|---|---|
| | 6 | 7 | 4 | 5 |
| EP-1 | 100 | | | |
| EP-2 | | 100 | | |
| Celloxide 2021(*1) | | | 100 | |
| Epikote 828(*2) | | | | 100 |
| TAAA(*3) | 0.5 | | 0.5 | |
| TEAACA(*4) | | 1 | | 0.5 |
| TPONBS(*5) | 3 | | 3 | |
| Glass transition Temperature (°C./DSC) | −23 | −10 | 160 | * |
| Tensile strength (kgf/mm2) | 0.3 | 1.2 | 4.2 | * |
| Tensile elongation (%) | 160 | 90 | 4 | * |

Note:
Celloxide 2021: 3,4-epoxycyrohexylmethyl-3',4'-epoxycyclohexanecarboxylate [manufactured by Daicel Chmeical Industries, Ltd.]
Epikote 828: epi-bis type epoxy resin [manufactured by Ciba-Geigy, Corp.]
TAAA: trisacetylacetonate aluminum
TEAACA: trisethylacetoacetato aluminum
TPONBS: triphenyl(o-nitrobenzyloxy)silcane
*: Incapable of measuring because of no-curing While the invention has been described in detail and with reference to specific embodiments thereof, it will be apparent to one skilled in the art that various changes and modifications can be made therein without departing from the spirit and scope thereof.

What is claimed is:

1. A composition which comprises one or a mixture of alicyclic compounds represented by formula (I)

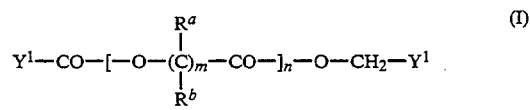

wherein $Y^1$ represents at least one of the structural groups

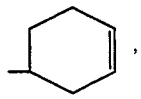

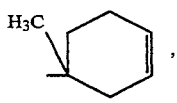

and

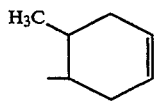

$R^a$ and $R^b$ each represents hydrogen or a methyl group, m represents a natural number of from 1 to 7, and n represents a natural number of from 1 to 20;

prepared by a process comprising reaction of a compound represented by formula (III)

$Y^1$—CO—O—CH$_2$—$Y^1$ (III)

with a lactone monomer under the presence of a catalyst.

2. A process for the preparation of a composition consisting essentially of one or a mixture of compounds represented by formula (I)

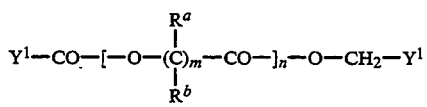  (I)

wherein $Y^1$ represents at least one of the structural groups

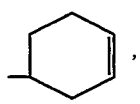,

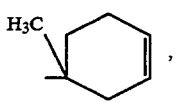, and

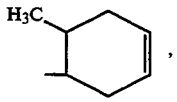, $R^a$ and $R^b$ each represents hydrogen or a methyl group, m represents a natural number of from 1 to 7, and n represents a natural number of from 1 to 20;

said process comprising reaction of a compound represented by formula (III)

$Y^1$—CO—O—CH$_2$—$Y^1$ (III)

wherein $Y^1$ is the same as defined above, with a lactone monomer under the presence of a catalyst.

3. A process as set forth in claim 2, wherein a compound having a hydroxyl group is added so as to provide a hydroxyl value of 0.01 to 50 in the composition obtained.

4. A process as set forth in claim 2, wherein said lactone compound is at least one compound selected from the group consisting of epsilon-caprolactone, trimethylcaprolactone, and beta-methyldelta valerolactone.

5. A process as set forth in claim 2, wherein a compound having at least one hydroxyl group is used together therewith.

6. A composition consisting essentially of one or a mixture of expoxized alicyclic compounds represented by formula (II)

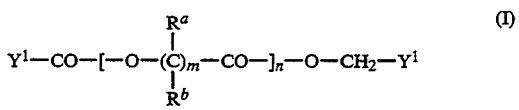  (II)

wherein $Y^2$ represents at least one of the structural groups

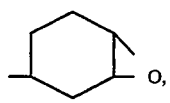,

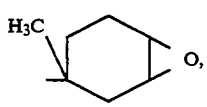, and

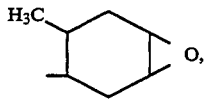, $R^a$ and $R^b$ each represents hydrogen or a methyl group, m represents a natural number of from 1 to 7, and n represents a natural number of from 1 to 20, prepared by a process comprising an epoxidation reaction of a composition which comprises a compound represented by formula (I)

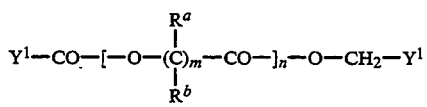  (I)

wherein $Y^1$ represents at least one of the structural groups

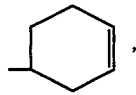,

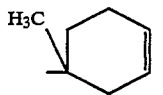,

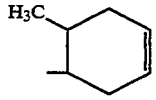, in the presence of an epoxidation agent, at a temperature from 0° to 70° C.

7. A process for the preparation of a composition which comprises one or a mixture of compounds represented by formula (II)

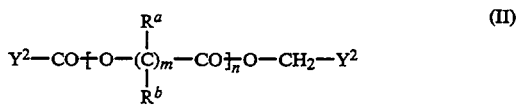  (II)

wherein $Y^2$ represents at least one of the structural groups

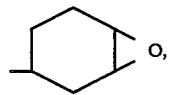,

-continued

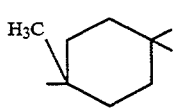

and

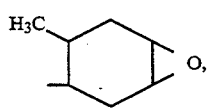

$R^a$ and $R^b$ each represents hydrogen or a methyl group, m represents a natural number of from 1 to 7, and n represents a natural number of from 1 to 20; said process comprising an epoxidation reaction of a composition which comprises a compound represented by formula (I)

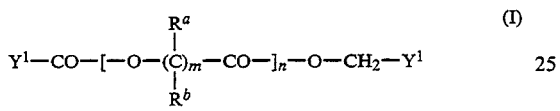

wherein $Y^1$ represents at least one of the structural groups

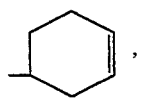

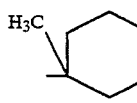

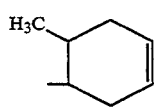

in the presence of an expoxidation agent, at a temperature of from 0° to 70° C.

8. A process as set forth in claim 7, wherein the epoxidation reaction is carried out in the presence of at least one additive selected from the group consisting of phosphoric acid, potassium phosphate, sodium phosphate, ammonium hydrogen phosphate, pyrophosphoric acid, potassium pyrophosphate, sodium pyrophosphate, 2-ethylhexyl pyrophosphate, potassium 2-ethylhexyl phosphate, sodium 2-ethylhexyl phosphate, tripolyphosphoric acid, potassium tripolyphosphate, and sodium tripolyphosphate.

9. A curable composition consisting essentially of a composition which comprises a compound represented by formula (II)

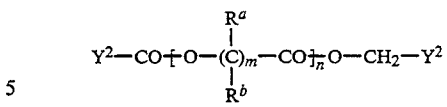

wherein $Y^2$ represents at least one of the structural groups

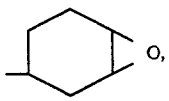

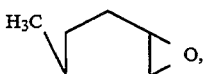

and

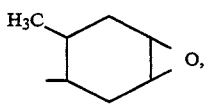

$R^a$ and $R^b$ each represents hydrogen or a methyl group, m represents a natural number of from 1 to 7, and n represents a natural number of from 1 to 20, and a curing agent for epoxy resins.

10. A photo-polymerizable composition consisting essentially of a composition which comprises a compound represented by formula (II)

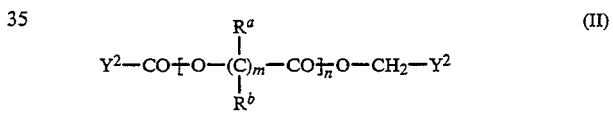

wherein $Y^2$ represents at least one of the structural groups

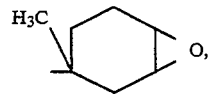

and

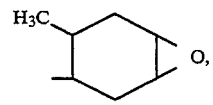

$R^a$ and $R^b$ each represents hydrogen or a methyl group, m represents a natural number of from 1 to 7, and n represents a natural number of from 1 to 20; and a photo-cationic polymerization initiator for epoxy resins.

* * * * *